United States Patent [19]

Marrot

[11] Patent Number: 5,721,333

[45] Date of Patent: Feb. 24, 1998

[54] NEW COMPOUNDS IN THE FORM OF 5,6-DIHYDROXYINDOLE POLYMERS, THEIR PROCESS OF PREPARATION AND COMPOSITIONS COMPRISING THEM

[75] Inventor: Laurent Marrot, Livry Gargan, France

[73] Assignee: L'Oreal, Paris, France

[21] Appl. No.: 548,195

[22] Filed: Oct. 25, 1995

[30] Foreign Application Priority Data

Oct. 25, 1994 [FR] France .................................. 94 12743

[51] Int. Cl.$^6$ .................................................. C08G 69/00
[52] U.S. Cl. ........................ 528/327; 528/337; 514/231.2
[58] Field of Search .......................... 514/231.2; 528/327, 528/337

[56] References Cited

U.S. PATENT DOCUMENTS 4,859,668   8/1989   Noga et al. ........................... 514/231.2

OTHER PUBLICATIONS

Marco d'Ischia et al., "Sulphydryl compounds in melanogenesis. Part I. Reaction of cysteine and glutathione with 5,6–dihydroxyindoles," Tetrahedron, 43(22):5351–5356 (1987). The month of publication is not available.

*Primary Examiner*—P. Hampton-Hightower
*Attorney, Agent, or Firm*—Finnegan, Henderson, Farabow, Garrett & Dunner, L.L.P.

[57] ABSTRACT

Novel 5,6-dihydroxyindole polymers, which are soluble in an aqueous or aqueous-alcoholic medium and a process for the preparation of these polymers and to compositions containing these polymers, especially cosmetic compositions.

19 Claims, No Drawings

NEW COMPOUNDS IN THE FORM OF 5,6-DIHYDROXYINDOLE POLYMERS, THEIR PROCESS OF PREPARATION AND COMPOSITIONS COMPRISING THEM

The invention is directed to novel compounds in the form of polymers of 5,6-dihydroxyindole, a process for their preparation and cosmetic compositions containing them.

Melanin compounds are generally known in the form of insoluble pigments. These are more particularly pigments which are the source of colouring of hair on the head, the skin, or hairs of human or animal origin. They may be prepared by synthesis, in particular by oxidation of indole derivatives, more particularly such as 5,6-dihydroxyindole.

The use of melanin pigments in cosmetics is subject to intense research on account of the fact that they are very similar to pigments existing in the natural state.

These melanin pigments are generally insoluble in water and in most of the solvents currently used in cosmetics. On account of their insolubility, the use of these pigments may pose certain problems such as the use of dispersing agents in order to obtain cosmetic compositions of good homogeneity.

Certain authors, such as Orlow, Osber and Paweleck [Pigment Cell Research 5, pages 113 to 121, (1992)], have described a method for obtaining a melanin pigment which is soluble in water at a pH above 5, starting with 5,6-dihydroxyindole-2-carboxylic acid (DHICA), alone or as a mixture with 5,6-dihydroxyindole (5,6-DHI). These soluble melanin pigments are, obviously, easier to use than insoluble pigments since they do not require the use of dispersing agents. However, they do not always retain satisfactory solubility after freeze-drying and redissolving.

Moreover, patent application WO 92/16189, the disclosure of which is specifically incorporated herein by reference, describes the preparation of a melanin pigment which is soluble in aqueous solution at a pH ranging between 5 and 9, starting with DHICA optionally combined with 5,6-DHI and/or with sulphur-containing compounds. According to that document, the presence of sulphur-containing compounds makes it possible to obtain soluble pigments having more varied colours. However, although these compounds are soluble, they do not have a satisfactory dyeing power.

The aim of the present invention is to solve these problems and to provide a novel 5,6-dihydroxyindole polymer which is soluble in an aqueous or aqueous-alcoholic medium, while at the same time having a satisfactory dyeing power.

The first subject of the present invention is thus a compound in the form of a 5,6-dihydroxyindole polymer substituted with at least one hydrophilic group attached to the polymer via a sulphur-containing residue, the number of hydrophilic groups being chosen so as to obtain a polymer which is soluble in an aqueous or aqueous-alcoholic medium.

It was observed that the polymer according to the invention is soluble, in particular, in an aqueous or aqueous-alcoholic medium having a pH of less than or equal to 7; that is to say a neutral pH or even an acidic pH, and that the polymer according to the invention retains good solubility in water or in an aqueous-alcoholic medium, even after freeze-drying and storage. It was also observed that this soluble 5,6-dihydroxyindole polymer is black in color and has good absorption in the visible region. The polymer according to the invention has a dyeing power which is comparable to, or even superior to, that of the soluble melanin polymers of the state of the art. The polymer according to the invention is furthermore very stable on storage after freeze-drying and may be redissolved.

Another subject of the present invention is a process for the preparation of a 5-6-dihydroxyindole polymer as defined above, in which:

an aqueous or aqueous-alcoholic solution, having a pH at least equal to 5, of a sulphur-containing compound containing hydrophilic groups, is prepared, 5,6-dihydroxyindole is added to this solution and the reaction is allowed to continue until the expected soluble 5,6-dihydroxyindole polymer is obtained; the amount of sulphur-containing compound used being chosen so that the final compound obtained is soluble in an aqueous or aqueous-alcoholic medium.

The compound according to the invention is thus in the form of a 5,6-dihydroxyindole polymer substituted with hydrophilic groups attached to the polymer via a sulphur-containing residue.

The compound according to the invention may consist of the product of a reaction between 5,6-dihydroxyindole and at least one sulphur-containing compound carrying hydrophilic groups.

The sulphur-containing compound is preferably chosen from compounds which contain at least one sulphur atom and which preferably cannot lead to either cyclization or substantial cyclization to benzothiazine by reaction with 5,6-dihydroxyindole.

Indeed, benzothiazines are intermediate compounds in the synthesis of phaeomelanins (reddish-brown-coloured melanins which photosensitize the skin). According to the invention, the cyclization to benzothiazine preferably cannot, or substantially cannot, take place, thereby removing the risks of a possible photosensitization of the skin.

Among these sulphur-containing compounds, there may preferably be mentioned sulphur-containing peptides containing hydrophilic groups such as reduced glutathione, or alternatively N-acetylcysteine. The amount of sulphur-containing compound present during the reaction is chosen so as to allow a final compound which is soluble in aqueous or aqueous-alcoholic media to be obtained. The concentration of the sulphur-containing compound used preferably ranges from 0.001 to 1% by weight approximately, relative to the total weight of the reaction medium.

The sulphur-containing compound is preferably predissolved in an aqueous or aqueous-alcoholic solution, or even an organic solution; the solution having a pH at least equal to 5. Indeed, it was observed that when the pH is below 5, the 5,6-dihydroxyindole cannot react with the sulphur-containing compound.

In order to adjust the pH, conventional acidifying or basifying agents such as hydrochloric acid and sodium hydroxide may be employed.

The pH of the solution preferably ranges from 5 to 10, and more preferably ranges from 6 to 8.

The concentration of 5,6-dihydroxyindole used may vary within wide proportions and preferably ranges from 0.001 to 10% by weight approximately, relative to the total weight of the reaction medium.

The 5,6-dihydroxyindole is preferably added in powder form, and the reaction is preferably carried out at a temperature above 0° C., and more preferably at a temperature ranging from 30° to 40° C. Even more preferably, the reaction temperature ranges from 36° to 38° C.

The reaction time required to obtain the final soluble compound may be of the order of 6 to 72 hours.

The reaction medium may also contain pH regulators, also referred to as "buffers", among which sodium phosphate may be mentioned.

A melanin compound is thus obtained in the form of a 5,6-dihydroxyindole polymer substituted with hydrophilic groups attached to the polymer via a sulphur-containing residue, the number of hydrophilic groups being chosen so that the compound is soluble in an aqueous or aqueous-alcoholic medium.

The solubility of this melanin compound in polymer form in the aqueous or aqueous-alcoholic medium preferably ranges from 50 to 100 mg/ml.

This compound may be used without further treatment in the form of an aqueous or aqueous-alcoholic solution, or it may be concentrated, or it may even be dried, for example by freeze-drying, so as to obtain a pulverulent product which may be used in cosmetic compositions.

Additional subjects of the present invention are the use of the melanin compounds in polymer form as defined above as a dye, in particular in cosmetic compositions, and the compositions obtained.

These soluble melanin compounds may in fact be incorporated without further treatment, concentrated and/or after freeze-drying, into cosmetic compositions of various types such as, for example, make-up compositions for the skin, the eyelashes or the eyebrows; compositions for protection of the human epidermis against UV radiation; and compositions for dyeing the hair.

In these compositions, the concentration of the melanin compounds preferably ranges from 0.001 to 5% by weight relative to the total weight of the composition.

When the compositions are used for making up the skin, the eyelashes or the eyebrows, for example as a skin treatment cream, a foundation, a stick of lipstick, an eyeshadow, a blusher, an eye-liner or a mascara, they may be in solid, liquid or pasty and anhydrous, or aqueous form, such as oil-in-water or water-in-oil emulsions, dispersions, lotions which are more or less thickened, sticks or powders. These compositions have the advantage of being entirely stable since it is not necessary to disperse the melanin compound on account of its solubility.

When the compositions are used for protecting the human epidermis against UV radiation, they constitute so-called antisun compositions and are generally in the form of emulsions such as creams and milks, ointments, gels, solid sticks or aerosol foams. The emulsions may also contain anionic, cationic, nonionic, amphoteric or zwitterionic surface-active agents and mixtures thereof.

When the compositions are used for dyeing the hair, they may be in the form of a shampoo, a lotion, a gel or a composition to be rinsed out, to be applied before or after shampooing, or before, during or after a permanent-waving or hair straightening operation, a styling or treating lotion or gel, a blow-drying or hair setting lotion or gel, a hair lacquer, a permanent-waving composition or a hair straightening composition.

The make-up compositions and the antisun compositions may also additionally contain at least one adjuvant chosen from fatty substances, organic solvents, silicones, thickeners, emollients, sunscreens, anti-foaming agents, moisturizing agents, fragrances, preserving agents, antioxidants, fillers, pigments, sequestering agents, treatment agents such as anionic, cationic, nonionic or amphoteric polymers or mixtures thereof, propellants and basifying or acidifying agents.

Among the fatty substances which may preferably be mentioned are oils, waxes, fatty acids, fatty alcohols, petrolatum, paraffin and lanolin, which are hydrogenated or acetylated.

The oils may preferably be chosen from animal, plant, mineral or synthetic oils and more preferably from hydrogenated palm oil, hydrogenated castor oil, liquid petrolatum, paraffin oil and purcellin oil.

The waxes may preferably be chosen from animal, plant, mineral or synthetic waxes. There may preferably be mentioned beeswax, carnauba wax, candelilla wax, sugarcane wax, Japan wax, ozokerites, montan wax, microcrystalline waxes, paraffins and silicone waxes.

Among the pigments which may preferably be mentioned are pearlescent and/or nacreous pigments which make it possible to vary the colors which may be obtained with the soluble melanin compounds of the invention or to increase the protection of the skin against ultraviolet radiation. In the latter case, metallic pigments such as the titanium, zinc, cerium or zirconium oxides may also be used.

It is also possible to combine the compound according to the invention with a compound such as DHA in cosmetic compositions. Indeed, if the hydrophilic groups of the compound according to the invention carry free amines, it is possible for them to promote the establishment of bridgings between the skin and/or the hair via compounds such as DHA. It is thus possible to obtain compositions for dyeing or coloring the skin and/or the hair.

The examples which follow are intended to illustrate the invention without, however, limiting the scope thereof.

EXAMPLE 1

10 mM of reduced glutathione were placed in a buffer solution at pH 7.5. The pH was adjusted to 7 by the addition of sodium hydroxide. 10 mM of 5,6-DHI powder were added and the reaction mixture was stirred for 48 to 72 hours at 37° C.

The compound obtained could not be separated by centrifugation at 15000 rev/min for 10 minutes. It was filtered through 0.22 μm pores and penetrated into a 1% agarose gel.

The filtered compound was freeze-dried according to the known techniques.

Immediately after freeze-drying, this compound redissolved in water when it was present at a concentration of 50 mg/ml.

After storage for 6 weeks at 4° C., the freeze-dried compound was still soluble in water for a concentration of 50 mg/ml.

EXAMPLE 2

5 mM of reduced glutathione were placed in a buffer solution at pH 7.5. The pH was adjusted to 7 by the addition of sodium hydroxide. 10 mM of 5,6-DHI powder were added and the reaction mixture was stirred for 48 to 72 hours at 37° C.

The compound obtained could not be separated by centrifugation at 15000 rev/min for 10 minutes. It was filtered through 0.22 μm pores and penetrated into a 1% agarose gel.

The filtered compound was freeze-dried according to the known techniques.

Immediately after freeze-drying, this compound redissolved in water for a concentration of 50 mg/ml.

EXAMPLE 3

15 mM of reduced glutathione were placed in a buffer solution at pH 7.5. The pH was adjusted to 7 by addition of sodium hydroxide. 20 mM of 5,6-DHI powder were added and the reaction mixture was stirred for 48 to 72 hours at 37° C.

The compound obtained could not be separated by centrifugation at 15000 rev/min for 10 minutes. It was filtered through 0.22 μm pores and penetrated into a 1% agarose gel.

The filtered compound was freeze-dried according to the known techniques.

Immediately after freeze-drying, this compound redissolved in water for a concentration of 50 mg/ml.

EXAMPLE 4

The optical density was measured at 475 nm and 600 nm for various compounds according to the invention, as solutions in water. This measurement was made at several concentrations.

The mass coefficient of absorption, which is the slope of the straight line obtained experimentally, was thus determined.

The following results were obtained:

a) for the compound of Example 1
 $\epsilon 475$ nm=6 $lg^{-1}cm^{-1}$ approximately
 $\epsilon 600$ nm=3.5 $lg^{-1}cm^{-1}$ approximately b) for the compound of Example 2
the mass coefficient values obtained were of the same order as for compound 1
 $\epsilon 475$ nm=6 $lg^{-1}cm^{-1}$ approximately
 $\epsilon 600$ nm=3.5 $lg^{-1}cm^{-1}$ approximately c) for the compound of Example 3, the values were lower:
 $\epsilon 475$ nm=3.7 $lg^{-1}cm^{-1}$ approximately
 $\alpha 600$ nm=2.2 $lg^{-1}cm^{-1}$ approximately This was quite probably due to a greater incorporation of glutathione into the 5,6-DHI polymer: for the same mass, the proportion of indole residues responsible for the absorption in the visible region was smaller.

The greater the absorption in the visible region, the more deeply coloured will be the melanin compound obtained and the better will be its dyeing power.

EXAMPLE 5

Precise amounts of compound obtained according to Example 1 were placed in water at 37° C., for 30 minutes.

The sample was divided into two parts, one of which was filtered through 0.45 µm or 0.22 µm pores.

Both parts of the sample were then brought to a concentration of 1 mg/ml and again left at 37° C., in order to dissolve the particles which may have been present therein.

The optical densities at 600 nm and 475 nm were compared.

The filterability was considered to reflect the solubility at a given concentration.

It was observed that:

for a concentration of 50 mg/ml, there was no retention of the compound on filtration.

for a concentration of 100 mg/ml, 95% of the compound was recovered after filtration through 0.45 µm pores. An identical result was obtained if the filtration operation was replaced by centrifugation at 15000 rev/min for 10 minutes.

After filtration through 0.22 µm pores, 87% of the compound was recovered.

It may thus be estimated that this compound has a solubility limit in water of the order of 100 mg/ml.

EXAMPLE 6

The light absorption of the compound obtained in Example 1 was compared with a compound according to the state of the art obtained by polymerization of DHICA at a concentration of 10 mM.

The absorption spectra were recorded for a solution of indole residues at a concentration of 50 µM in water.

The following results were obtained:

|  | 350 nm | 400 nm | 500 nm | 600 nm |
|---|---|---|---|---|
| absorption of the compound according to the invention | 0.23 | 0.18 | 0.1 | 0.08 |
| absorption of DHICA | 0.3 | 0.1 | 0.05 | 0.03 |

The same measurements were made for a compound according to the invention obtained from 5 mM of 5,6-DHI and 5 mM of glutathione, compared with a compound obtained from 5 mM of DHICA.

The following results were obtained:

|  | 350 nm | 400 nm | 500 nm | 600 nm |
|---|---|---|---|---|
| absorption of the compound according to the invention | 0.24 | 0.18 | 0.1 | 0.09 |
| absorption of DHICA | 0.24 | 0.11 | 0.05 | 0.02 |

It was thus observed that the compounds according to the invention absorbed more in the visible region than the compounds of the state of the art.

This is reflected in the production of a deeper, more intense colour when a composition comprising the compound according to the invention was used.

What is claimed is:

1. A 5,6-dihydroxyindole polymer substituted with at least one hydrophilic group via a sulphur-containing residue, wherein the number of hydrophilic groups in said polymer is such that said polymer is soluble in an aqueous or aqueous-alcoholic medium.

2. A 5,6-dihydroxyindole polymer according to claim 1, which is soluble in an aqueous or aqueous-alcoholic medium having a pH of less than or equal to 7.

3. A 5,6-dihydroxyindole polymer according to claim 1, which has a solubility in said medium ranging from 50 to 100 mg/ml.

4. A 5,6-dihydroxyindole polymer according to claim 1, said polymer being prepared by the reaction between 5,6-dihydroxyindole and a sufficient amount of at least one sulphur-containing compound containing hydrophilic groups.

5. A 5,6-dihydroxyindole polymer according to claim 4, wherein said at least one sulphur-containing compound contains at least one sulphur atom and does not cyclize 5,6-dihydroxyindole to benzothiazine.

6. A 5,6-dihydroxyindole polymer according to claim 4, wherein said at least one sulphur-containing compound is N-acetylcysteine or a sulphur-containing peptide containing hydrophilic groups.

7. A 5,6-dihydroxyindole polymer according to claim 4, wherein said at least one sulphur-containing compound is reduced glutathione.

8. A 5,6-dihydroxyindole polymer according to claim 1, which is in the form of an aqueous or aqueous-alcoholic solution, in concentrated form or in pulverulent form.

9. A process for the preparation of a 5,6-dihydroxyindole polymer, which comprises the steps of:

preparing an aqueous or aqueous-alcoholic solution containing at least one sulphur containing compound containing hydrophilic groups, wherein said aqueous or aqueous-alcoholic solution has a pH at least equal to 5, and adding 5,6-dihydroxyindole to said aqueous or aqueous-alcoholic solution and reacting for a time sufficient to obtain a soluble 5,6-dihydroxyindole polymer, the amount of said sulphur-containing compound being sufficient to render said 5,6-dihydroxyindole polymer soluble in said aqueous or aqueous-alcoholic medium and said hydrophilic groups being attached to said polymer through a sulphur-containing residue.

10. A process according to claim 9, wherein said at least one sulphur-containing compound contains at least one sulphur atom and does not cyclize 5,6-dihydroxyindole to benzothiazine.

11. A process according to claim 9, wherein said at least one sulphur-containing compound is N-acetylcysteine or a sulphur-containing peptide carrying hydrophilic groups.

12. A process according to claim 9, wherein said at least one sulphur-containing compound is reduced glutathione.

13. A process according to claim 9, wherein the concentration of said at least one sulphur-containing compound containing hydrophilic groups ranges from 0.001 to 1% by weight relative to the total weight of the reaction medium.

14. A process according to claim 9, wherein the concentration of said 5,6-dihydroxyindole ranges from 0.001 to 10% by weight relative to the total weight of the reaction medium.

15. A process according to claim 9, wherein said 5,6-dihydroxyindole is added to said aqueous or aqueous-alcoholic solution in powder form.

16. A process according to claim 9, wherein said reaction is carried out at a temperature greater than 0° C.

17. A process according to claim 16, wherein said reaction is carried out at a temperature which ranges from 30° C. to 40° C.

18. A process according to claim 9, wherein the pH of said aqueous and/or aqueous-alcoholic solution ranges from 5 to 10.

19. A process according to claim 18, wherein the pH of said aqueous and/or aqueous-alcoholic solution ranges from 6 to 8.

* * * * *